United States Patent [19]

Anderson et al.

[11] Patent Number: 5,459,193
[45] Date of Patent: Oct. 17, 1995

[54] POLYSTYRENE-ETHYLENE/BUTYLENE-POLYSTYRENE HOT MELT ADHESIVE

[75] Inventors: Carolyn M. Anderson, Stillwater; Eugene R. Simmons, Vadnais Heights, both of Minn.

[73] Assignee: H. B. Fuller Licensing & Financing, Inc., Wilmington, Del.

[21] Appl. No.: 393,242

[22] Filed: Feb. 23, 1995

Related U.S. Application Data

[63] Continuation of Ser. No. 134,933, Oct. 12, 1993, abandoned.

[51] Int. Cl.[6] .................................................. C08L 53/02
[52] U.S. Cl. .............................................. 524/505; 525/98
[58] Field of Search ................................ 524/505; 525/98

[56] References Cited

U.S. PATENT DOCUMENTS

| | | | |
|---|---|---|---|
| 3,652,474 | 3/1972 | Berry et al. | 260/27 EV |
| 4,136,699 | 1/1979 | Collins et al. | 128/290 |
| 4,369,284 | 1/1983 | Chen | 524/476 |
| 4,411,058 | 10/1983 | Chen | 29/571 |
| 4,569,124 | 2/1986 | Rensch et al. | 29/591 |
| 4,618,213 | 10/1986 | Chen | 350/96.34 |
| 4,813,947 | 3/1989 | Korpman | 604/387 |
| 4,833,193 | 5/1989 | Sieverding | 524/486 |
| 5,085,655 | 2/1992 | Mann et al. | 604/389 |
| 5,149,741 | 9/1992 | Alper | 525/95 |
| 5,153,254 | 10/1992 | Chen | 524/505 |
| 5,204,390 | 4/1993 | Szymanski et al. | 524/91 |
| 5,239,723 | 8/1993 | Chen | 15/104.002 |
| 5,262,468 | 11/1993 | Chen | 524/476 |

FOREIGN PATENT DOCUMENTS

| | | |
|---|---|---|
| 2049168 | 2/1992 | Canada. |
| 0428017A2 | 10/1990 | European Pat. Off.. |
| 0471384A1 | 8/1991 | European Pat. Off.. |

OTHER PUBLICATIONS

What is KRATON® Rubber.

*Primary Examiner*—James J. Seidleck
*Assistant Examiner*—I. Zemel
*Attorney, Agent, or Firm*—Merchant, Gould, Smith, Edell, Welter & Schmidt

[57] ABSTRACT

An improved hot melt adhesive with low self-adhesion. The adhesive is useful for disposable articles and employs a S-EB-S block copolymer. The adhesive does not require a release liner and has superior stay-in-place properties.

8 Claims, 2 Drawing Sheets

POLYSTYRENE-ETHYLENE/BUTYLENE-POLYSTYRENE HOT MELT ADHESIVE

This is a continuation application Ser. No. 08/134,933, Oct. 12, 1993, now abandoned.

FIELD OF THE INVENTION

This invention relates to hot melt adhesives comprising a high molecular weight polystyrene-ethylene/butylene-polystyrene block copolymer and articles constructed therefrom. This invention particularly relates to certain improved positioning adhesive formulations for disposable articles such as sanitary napkins, incontinent pads, bed pads, and feminine pads, where an adhesive layer is used to attach the article to a woven fabric substrate, such as an undergarment or bed sheet.

BACKGROUND OF THE INVENTION

Block copolymers have been used in the hot melt adhesive industry for a variety of applications. Block copolymers are often the preferred polymer base due to their good heat stability, high cohesive strength, and compatibility with a wide range of tackifiers and plasticizers.

Kraton G-1651, a high molecular weight S-EB-S linear A-B-A block copolymer, having a molecular weight of about 240,000, has been used in the past by the injection molding industry for shoe soles. Due to its high molecular weight, it is believed that it has not been previously used by the hot melt adhesive industry.

The use of hot melt adhesives comprised of conventional molecular weight block copolymers for purposes of adhering an absorbent article, such as a sanitary napkin, to an undergarment is known. Raykovitz et al., U.S. Pat. No. 4,704,110 teaches an absorbent article utilizing an adhesive with a S-B-S multi-block A-B-A-B-A-B copolymer. Nelson et al. EP 0,525,251, teaches an improved positioning adhesive including a S-I-S linear A-B-A block copolymer containing at least 25 parts styrene. Collins et al., U.S. Pat. No. 4,136,699 teaches a conventional molecular weight S-EB-S linear A-B-A block copolymer based construction and positioning adhesive for absorbent articles. The prior art, to date, has not shown the use of a high molecular weight S-EB-S in hot melt adhesives.

A positioning adhesive is commonly applied to a release liner and transfer coated to the garment facing surface of an article such as a sanitary napkin. Upon removal of the release liner, it is common for the adhesive to accidentally come in contact with itself prior to placement on the undergarment. This is particularly a problem with winged products. When the positioning adhesives' composition is in accordance with the teachings of Raykovitz, Nelson, or Collins, the positioning adhesive is of such high self adhesion (in excess of the strength of the garment facing surface) that the adhesive layers are separable only at the expensive of destroying the article. Thus there is a need for an adhesive which adheres adequately to an undergarment, yet can be separated from itself.

Another problem associated with prior art positioning adhesives concerns "stay in place" properties. Under conditions of low pressure, the positioning adhesive tends to lose adhesion to the undergarment. In many instances this loss of adhesion causes the sanitary napkin to shift from its original position or become unattached from the undergarment entirely.

SUMMARY OF THE INVENTION

It is therefore an object of this invention to provide an improved positioning adhesive with low self adhesion, thereby being able to be removed from itself without destroying the article. Further, another object of this invention is to provide a pressure sensitive adhesive that may be used with or without release paper on articles that traditionally incorporate such release paper. The present adhesive also has superior stay-in-place properties.

The present invention is a hot melt adhesive comprising a S-EB-S block copolymer having a molecular weight greater than about 200,000 as measured by Gel Permeation Chromatography, with values reported relative to polystyrene standards. In the present invention, it has been found that a high molecular weight S-EB-S block copolymer provides surprising properties in a hot melt adhesive. The high molecular weight S-EB-S polymer can be used in place of conventional molecular weight S-EB-S block copolymers at lower concentrations in a variety of applications where high cohesive strength is an important parameter.

DETAILED DESCRIPTION OF THE INVENTION

Typically, disposable articles such as sanitary napkins, incontinent pads, bed pads, or feminine pads utilize an adhesive which attaches the article to a woven fabric substrate, such as an undergarment or bedsheet. Prior to this invention, the adhesive would be covered with a release liner, which was typically a silicon coated paper or some type of low surface energy polymeric film. When the user would remove the article from its packaging, the release liner would be peeled away and the article would be positioned on a target surface, typically an undergarment or bedpad. The requirement of release paper is undesirable both from a cost standpoint and an environmental standpoint. The release paper, after being peeled away from the article, serves no purpose and thus must be discarded.

The adhesive of the present invention avoids the requirement of release paper, in that it has low self adhesion. In other words, the adhesive may be folded over upon itself and thereafter be peeled apart successfully. The adhesive has the strength to secure the article to its target surface, but has self-adhesion properties which do not exceed the tear strength of the article. The ability of the adhesive to fold upon itself defeats the need for release paper. When the user thereafter prepares to place the article on the target surface, the article is unfolded such that the adhesive is not folded upon itself. Thereafter, the article is placed on the target surface.

Prior adhesives could not be successfully folded over to achieve such an article. The prior adhesives were so tacky from a practical standpoint, they could not be peeled apart without destroying the article. Prior to the present invention, if the adhesive was made such that it was not tacky, the adhesive characteristics diminished to such a point that it could not effectively be used to adhere the article to the target surface. In other words, the adhesive was not tacky enough to provide the required adhesion between the target surface and the article.

Figure 1:
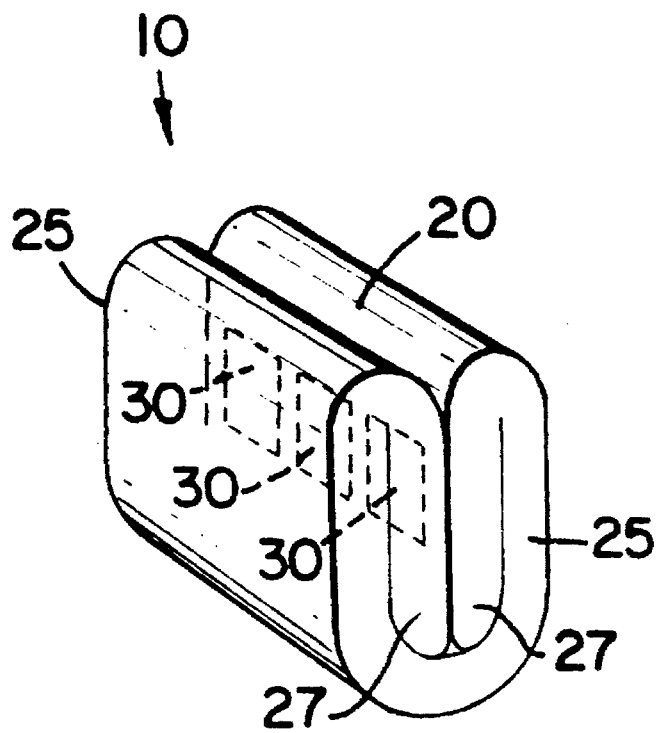
FIG. 1 is a perspective view of a disposable article such as a panty liner folded upon itself.

FIG. 1 illustrates one of the embodiments of the product of this invention. Panty liner 10 has two transverse edges 25 and two longitudinal edges 27. Panty liner 10 also has one or more areas of attachment 30 which serve to maintain panty liner 10 in the folded configuration prior to use.

Figure 2:
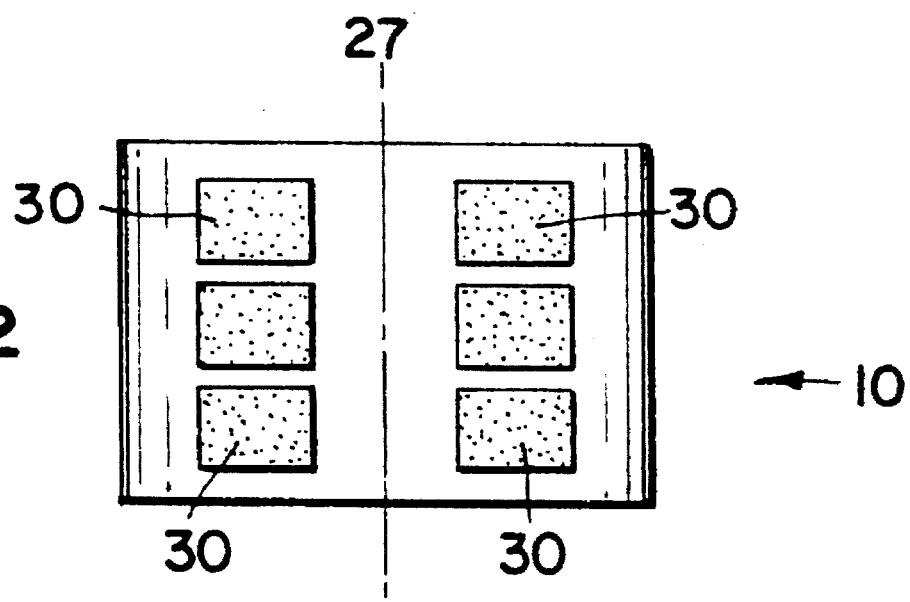
FIG. 2 is the panty liner of FIG. 1 unfolded.

FIG. 2 illustrates the embodiment depicted in FIG. 1 after it has been opened. In this view, the actual areas in which attachment means 30 are located can be seen. Choosing the patterns of attachment means 30 on the garment facing side 20 of the panty liner so that they would contact each other when the article is folded eliminates the need for release paper on the garment facing side of panty liner 10. The adhesion areas 30 should completely cover one another. Thus, as shown in FIG. 1, each attachment means 30 is placed in an alternating pattern with another attachment means. Attachment means 30 comprises the adhesive of the present invention. The adhesive may be on a supported adhesive strip or applied directly to a permeable back sheet or a surface modified polyolefin.

Figure 3:
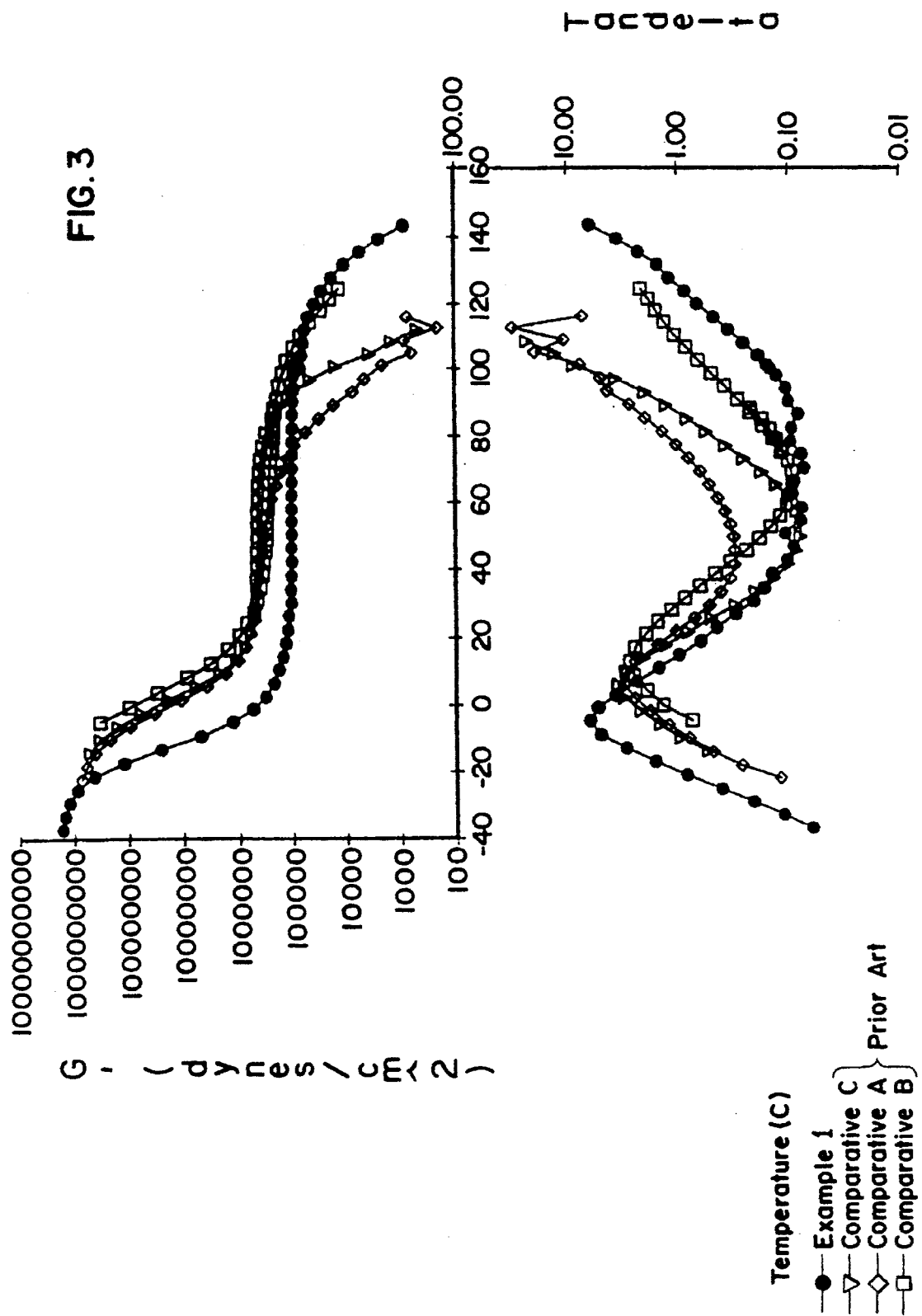
FIG. 3 is rheology data of the prior art and the present invention.

FIG. 3 illustrates the present invention's advantage over the prior art. Example 1 is compared to comparative Examples A, B, and C. The prior art illustrates a balance of tack and shear strength that requires a high modulus at room temperature in order to maintain enough cohesive strength. (G', G" crossover 80° C. to 100° C.). In contrast, the present invention allows for lower G' at room temperature and therefore better tack properties while maintaining a higher than normal crossover point (110° C. and above). In other words, the present invention has high tack and high cohesive strength rather than having to sacrifice one for the other.

The Adhesive

The major component of the adhesive of this invention, present in the amount of about 5 to 20% by weight, preferably in an amount of about 5 to 15% by weight for superior positioning properties, and most preferably in an amount of about 8 to 12% by weight for superior low self adhesion, comprises a S-EB-S linear A-B-A block copolymer having a molecular weight in excess of about 200,000. Polymers of this type, such as Kraton G-1651, commercially available from Shell Corporation, are not intended for the hot melt adhesive industry, but rather directed at the injection molding industry. Therefore, typical technical information relating to adhesive performance properties is unknown.

As described above, the present invention results in a superior adhesive with at least two beneficial properties. The adhesive has superior positioning properties, which result in excellent stay-in-place properties. When the article is positioned on the target surface, it will stay in position much better than prior adhesives. Further, the present invention also is a low self adhesion adhesive, as described above.

We have found the above S-EB-S block copolymer may also have added thereto, a compatible A-B-A block copolymer, A-B-A-B-A multiblock copolymer or radial block copolymer thermoplastic resins. Such A-B-A block copolymers are disclosed in Collins, U.S. Pat. No. 4,136,699. In the present invention, an A-B-A block copolymer available under the tradename Kraton 6-1654, commercially available from Shell Corporation is preferred. In a preferred composition, 0–15 weight percent of an A-B-A block copolymer is useful, a more preferred composition of 0–10 weight percent and a most preferred composition of 0–6 weight percent is useful. The additional block copolymer is preferred, but not necessary.

Tackifying Resin

The adhesives of the invention preferably contain a tackifying resin. Tackifying resins may be present in an amount from 0 to 60 percent by weight. Preferably the resin is present in an amount of 30 to 60 weight percent. Tackifying resins useful in the adhesives of the invention comprise rosin derivatives including wood rosin, tall oil, tall oil derivatives, rosin ester resins, natural and synthetic terpenes and aliphatic aromatic or mixed aliphatic-aromatic tackifying resins. Aromatic monomers useful in forming the aromatic containing resin compositions of this invention can be prepared from any monomer containing substantial aromatic qualities and a polymerizable unsaturated group. Typical examples of such aromatic monomers include styrenic monomers, styrene, alphamethyl styrene, vinyl toluene, methoxy styrene, tertiary butyl styrene, chlorostyrene, etc., indene monomers including indene, methyl indene and others. Aliphatic monomers are typically natural and synthetic terpenes which contain $C_6$ and $C_5$ cyclohexyl or cyclopentyl saturated groups that can additionally contain a variety of substantial aromatic ring substituents. Aliphatic tackifying resins can be made by polymerizing a feed stream containing sufficient aliphatic monomers such that the resulting resin exhibits aliphatic characteristics. Such feed streams can contain other aliphatic unsaturated monomers such as 1,3-butadiene, cis-1,3-pentadiene, trans-1,3-pentadiene, 2-methyl-11,3-butadiene, 2-methyl-2-butene, cyclopentadiene, dicyclopentadiene, terpene monomer, terpene phenolic resins and others. Mixed aliphatic aromatic resins contain sufficient aromatic monomers and sufficient aliphatic monomers to produce a resin having both aliphatic and aromatic character. The article by Davis, "The Chemistry of $C_5$ Resins," discusses synthetic $C_5$ resin technology. The preferred tackifying agent is a hydrogenated $C_5$ resin.

Representative examples of useful aliphatic resins include hydrogenated synthetic $C_9$ resins, synthetic branched and unbranched $C_5$ resins and mixtures thereof. Representative examples of aromatic tackifying resins include styrenated terpene resins, styrenated $C_5$ resins or mixtures thereof.

The adhesive compositions of the invention can contain rosin and rosin derivatives as a tackifying agent. Rosin is a solid material that occurs naturally in the oleo rosin of pine trees and typically is derived from the oleo resinous exudate of the living tree, from aged stumps and from tall oil produced as a by-product of kraft paper manufacture. After it is obtained, rosin can be treated by hydrogenation, dehydrogenation, polymerization, esterification, and other post treatment processes. Rosin is typically classed as a gum rosin, a wood rosin, or as a tall oil rosin which indicates its source. The materials can be used unmodified, in the form of esters of polyhydric alcohols, and can be polymerized through the inherent unsaturation of the molecules. Materials are commercially available and can be blended into the adhesive compositions using standard blending techniques. Representative examples of such rosin derivatives include pentaerythritol esters of tall oil, gum rosin, wood rosin, or mixtures thereof.

Specific examples of useful tackifying resins that can be compatible with the adhesives of the invention include materials such as natural and modified rosins, glycerol, and pentaerythritol esters of natural and modified rosins, copolymers and terpolymers of natural terpenes, polyterpene resins having a softening point as determined by ASTM method E28-58 T, of from about 80° C. to 150° C., phenolic modified terpene resins and hydrogenated derivatives thereof; aliphatic petroleum hydrocarbon resins having a ring and ball softening point of from about 70° C. to 135° C., aromatic petroleum hydrocarbon resins and hydrogenated derivatives thereof and alicyclic petroleum hydrocarbon resins and the hydrogenated derivatives thereof. Liquid resins are also envisioned, thus the softening points are irrelevant for liquids.

Plasticizers

A plasticizer is broadly defined as a typically organic composition that can be added to thermoplastics, rubbers and other resins to improve extrudability, flexibility, workability, or stretchability.

Plasticizing oils are used in the adhesive of the invention. Preferably, the plasticizing agent is a liquid at ambient temperature, such as hydrocarbon oils or polybutene, and is present in an amount of about 20 to 95% by weight of the adhesive. More preferably, the plasticizer is in an amount of 30 to 50 weight percent. Such oils are primarily hydrocarbon oils low in aromatic content and are paraffinic or naphathenic in character. The oils are preferably low in volatility, are clear and have as little color and odor as possible. The use of a plasticizing oil in this invention also contemplates the use of olefin oligomers, polybutene low molecular weight polymers, vegetable oils and their derivatives and similar plasticizing liquids.

As is known in the art, various other components can be added to modify the tack, color, odor, etc., of a hot melt adhesive. It is generally preferred that the other components or ingredients should be relatively inert and have negligible effects upon the properties contributed by the block copolymer, tackifying agent, and plasticizing oil. Antioxidants and other stabilizing ingredients can also be added to protect the adhesive from various heat and light induced degradation, but are not essential to the compositions of this invention.

TEST METHODS

This test method describes how to measure the removal force of an adhesive surface bonded to itself.

Material and Equipment

1. Mechanical roll-down device with 4½ lb. roller. Available through: Engineering Service Glenview, Ill. 60025
2. Slip Peel Tester Available through: Instrumentors, Inc. P.O. Box 36056 Cleveland, Ohio 44136 Telephone: (216) 238-3430

The first step is to prepare hot melt coated adhesive films on Mylar (TMHM-156) or polyethylene (TMHM-156P) film using an Acumeter or Meltex coater at an appropriate application temperature. The coat weight is checked as in TMHM-008 with a target coat weight of 50 g/m2±3 g/m2.

The adhesive coated Mylar is cut into two dimensions: 1 inch×4 inches in machine direction and 1½ inches×4 inches in machine direction. At one end of each strip, fold ¼" of the strip onto itself length-wise to create a grip. Remove the release paper and place the adhesive surface of one 1" wide strip onto the adhesive surface of one 1½ wide strip with the grips at the same end. Place the composite on the mechanical roll-down device, and allow the roller two passes over the sample, one forward and one back. A timer is activated and the sample is placed into the jaws of the slip-peel tester. The 1" wide strip is placed into the jaw that moves and the 1½" wide strip is placed into the jaw which is stationary. No more than one minute after the sample has been removed from the roll-down device, the sample is peeled at 12 ipm, averaging over 10 seconds. The procedure is repeated five times, recording the average T-peel value and noting any legging or adhesive transfer. The t-peel values are reported in grams per lineal inch.

The above test method is modified to measure the removal force of an adhesive surface that has been laminated to itself for a period of time under conditions of elevated temperature and humidity. The test is repeated, but the sample is placed in an envelope and incubated at 120° F. and 50% RH for one week. The samples are thereafter tested as above, with the results reported below as laminates.

In the disposable article industry, it is preferred to have an initial t-peel to cotton in the range of about 100–500, most preferred about 200–500 grams per lineal inch. The stressed t-peel should be equal to or less than the initial t-peel. In order to achieve preferred stay-in-place properties, the initial t-peel value should be as close as possible to the delayed t-peel value. This indicates there is no loss of adhesion over time.

With regard to self peel, it is preferred to have a value of less than about 200, most preferably less than about 100 grams per lineal inch. Values greater than 200 grams per lineal inch often result in substrate or backing failure of the article.

EXAMPLES

The following examples were made to demonstrate the superior properties of the present invention. Three comparative examples were made according to the teachings of the prior art. These are shown in Table 1. Table 2 illustrates three examples made with Example 1 and 3 being made according to the preferred teachings of the present invention.

Table 3 illustrates the comparison between the prior art and the present invention.

TABLE 1

| Ingredient | Tradename | Percent By Weight |
|---|---|---|
| Comparative A (Raykovitz et al., U.S. Pat. No. 4,704,110) | | |
| A-B-A Block Copolymer | Stereon 840A | 30.0 |
| Plasticizing Oil | 500 Second Oil | 20.0 |
| Tackifying Resin | Zonatac 105 Lite | 49.5 |
| Antioxidant | Irganox 1010 | 0.5 |
| Comparative B (Collins et al., U.S. Pat. No. 4,136,099) | | |
| A-B-A Block Copolymer | Kraton G-1650 | 15.3 |
| Plasticizing Oil | 1200 Second Oil | 28.0 |
| Tackifying Resin | Wingtack 95 | 53.5 |
| Antioxidant | Irganox 1010 | .1 |
| Antioxidant | Irganox 1076 | .1 |
| Pigment | PMS-04110-PHM | 3.0 |
| Comparative C (Nelson et al., EP No. 0,525,251) | | |
| A-B-A Block Copolymer | Vector 4411 | 30.0 |
| Plasticizing Oil | Kaydol Oil | 20.0 |
| Tackifying Resin | Zonatac 105 Lite | 49.0 |
| Antioxidant | Irganox 1010 | 1.0 |

TABLE 2

| Ingredient | Example 1 | Example 2 | Example 3 |
| --- | --- | --- | --- |
| Kraton G-1651 | 10.0% | — | 6.0% |
| Kraton G-1654 | — | 10.0 | 4.0 |
| Escorez 5380 | 49.8 | 49.8 | 49.5 |
| Escorez 2520 | — | — | — |
| ECR-177 | — | — | — |
| N-500-HT Oil | 40.0 | 40.0 | 40.0 |
| Irganox 1010 | .1 | .1 | .1 |
| Irganox 1076 | .1 | .1 | .1 |

All samples were made using a sigma blade mixer with standard hot melt blending techniques.

TABLE 3

|  | Comparative "A" | Comparative "B" | Comparative "C" | Example 1 | Example 2 | Example 3 |
| --- | --- | --- | --- | --- | --- | --- |
| Initial T-peel to Cotton | 526 +/− 52 | 451 +/− 44 | 192 +/− 13 | 291 +/− 34 | 240 +/− 35 | 291 +/− 19 |
| Delayed T-peel to Nylon | 522 +/− 39 | 277 +/− 17 | 135 +/− 18 | 297 +/− 6.5 | 127 +/− 7.0 | 290 +/− 19 |
| Initial T-peel to Nylon | 806 +/− 111 | 526 +/− 47 | 456 +/− 37 | 287 +/− 21 | 92 +/− 4.9 | 251 +/− 25 |
| Stressed T-peel to Nylon | 739 +/− 58 | 333 +/− 33 | 208 +/− 7.6 | 100 +/− 15 | 98 +/− 9.1 | 150 +/− 28 |
| Self T-peel | 523 +/− 24 | 702 +/− 65 | 390 +/− 27 | 46 +/− 4.7 | 43 +/− 13 | 61.5 +/− 5.9 |
| Laminate T-peel | * | * | * | 95 +/− 4.7 | 1487 +/− 367 | 124 +/− 1.8 |
| Viscosity @ 300° F. | 12,375 cps | 17,000 cps | 4,720 cps | 23,500 cps | 6620 cps | 9000 cps |
| Viscosity @ 325° F. | 7,375 cps | 4,500 cps | 2,730 cps | 6,500 cps | 3145 cps | 3525 cps |
| Viscosity @ 350° F. | 4,840 cps | 1,850 cps | 1,365 cps | 3,000 cps | 1815 cps | 1910 cps |

*The laminate T-peel was not tested on the comparative sample because their self T-peel values are greater than 200 g.

This table illustrates the utility and uniqueness of incorporating high molecular weight S-EB-S polymers, such as Kraton G-1651, in positioning adhesive formulations. Example 2 is the identical formula as Example 1 with the exception of substituting Kraton G-1654, having a molecular weight of 180,000, in place of Kraton G-1654. Although the self T-peel values are very similar to Example 1, the laminate T-peel values are extremely high.

Example 3 represents the advantage of blending Kraton G-1651 in order to reduce the viscosity. Examples 1 & 3 are both preferred formulations due to their low self T-peel and low laminate T-peel values.

The present invention is not limited to the examples and embodiments set forth above. As will be understood by those of ordinary skill in the art, alternate embodiments, variations and modifications of the present invention are envisioned.

We claim:

1. A hot melt adhesive composition comprising:

(a) about 5 to 20 percent by weight of a S-EB-S block copolymer having a molecular weight greater than about 200,000;

(b) about 20 to 95 weight percent of a plasticizer; and (c) up to about 60 weight percent by weight of a solid tackifying agent.

2. The hot melt adhesive of claim 1 wherein said S-EB-S block copolymer is present in an amount of about 5 to 15 percent by weight.

3. The hot melt adhesive of claim 1 wherein said S-EB-S block copolymer is present in an amount of about 8 to 12 percent by weight.

4. The hot melt adhesive of claim 3 exhibiting low self adhesion, with self t-peel values of less than about 200 grams per lineal inch.

5. The hot melt adhesive of claim 1 wherein said plasticizer is selected from the group consisting of liquid C5 resins, hydrogenated C5 resins, styrenated C5 resins, styrenated terpene resins, hydrogenated C9 resins, rosin derivatives, napthenic oil, paraffinic oil, polybutene and mixtures thereof.

6. The hot melt adhesive of claim 1 wherein said tackifying agent is selected from the group consisting of C5 resins, hydrogenated C5 resins, styrenated C5 resins, styrenated terpene resins, hydrogenated C9 resins, rosin derivatives and mixtures thereof.

7. A hot melt positioning adhesive comprising:

(a) 5–15 percent by weight of a S-EB-S block copolymer having a molecular weight of greater than 200,000;

(b) 30 to 95 percent of a compatible plasticizer selected from the group consisting of liquid C5 resins, hydrogenated C5 resins, styrenated C5 resins, styrenated terpene resins, hydrogenated C9 resins, rosin derivatives, napthenic oil, paraffinic oil, polybutene and mixtures thereof; and (c) up to about 60 percent by weight of a solid tackifying agent selected from the group consisting of C5 resins, hydrogenated C5 resins, styrenated C5 resins, styrenated terpene resins, hydrogenated C9 resins, rosin derivatives and mixtures thereof.

8. A hot melt pressure sensitive adhesive comprising:

(a) about 8 to 12 percent by weight of a S-EB-S block copolymer having a molecular weight greater than 200,000;

(b) about 30–50 percent by weight of a plasticizer selected from the group consisting of napthenic plasticizing oil, paraffinic plasticizing oil or mixtures thereof;

(c) about 30–60 percent by weight of a tackifying agent selected form the group consisting of $C_5$ resins, hydrogenated $C_5$ resins, hydrogenated $C_9$ resins and mixtures thereof;

said adhesive exhibiting a self t-peel of less than about 200 grams per lineal inch.

* * * * *

UNITED STATES PATENT AND TRADEMARK OFFICE
CERTIFICATE OF CORRECTION

PATENT NO. : 5,459,193

DATED : October 17, 1995

INVENTOR(S) : Anderson et al.

It is certified that error appears in the above-identified patent and that said Letters Patent is hereby corrected as shown below:

On column 1, line 57, please delete "expensive" and substitute therefore --expense--

On column 5, line 62, please delete "1 1/2" and substitute therefore --1 1/2"--

On column 8, line 13, please delete "6620 cps" and substitute therefore --6,620 cps--

On column 8, line 15, please delete "3145 cps" and substitute therefore --3,145 cps--

On column 8, line 17, please delete "1815 cps" and substitute therefore --1,815 cps--

On column 8, line 13, please delete "9000 cps" and substitute therefore --9,000 cps--

On column 8, line 15, please delete "3525 cps" and substitute therefore --3,525 cps--

On column 8, line 17, please delete "1910 cps" and substitute therefore --1,910 cps--

Signed and Sealed this

Thirteenth Day of February, 1996

Attest:

BRUCE LEHMAN

Attesting Officer

Commissioner of Patents and Trademarks